United States Patent [19]

Debabov et al.

[11] 4,321,325

[45] Mar. 23, 1982

[54] PROCESS FOR PRODUCING L-THREONINE

[76] Inventors: Vladimir G. Debabov, ulitsa Miklukho-Maklaya, 43, kv. 57; Nelli I. Zhdanova, Leningradskoe shosse, 112, korpus 3, kv. 748; Alexandr K. Sokolov, Levshinsky, Maly pereulok, 14/9, kv. 113; Vitaly A. Livshits, ulitsa Kirovogradskaya, 24, korpus 3, kv. 8; Jury I. Kozlov, Yasenevo, Vtoroi mikroraion, korpus 3, kv. 178; Evgeny M. Khurges, ulitsa Tikhvinskaya, 1/13, kv. 16; Nikolai K. Yankovsky, ulitsa Radischevskaya, 13/15, kv. 59; Mikhail M. Gusyatiner, ulitsa Chertanovskaya, 8, korpus 1, kv. 66; Albert F. Sholin, Teply Stan, 1a mikroraion, korpus 18, kv. 100; Viktor P. Antipov, Suschevsky val, 22, kv. 28; Tamara M. Pozdnyakova, ulitsa Dorozhnaya, 20, korpus 3, kv. 50, all of Moscow, U.S.S.R.

[21] Appl. No.: 133,284

[22] Filed: Mar. 24, 1980

[30] Foreign Application Priority Data

Jul. 13, 1978 [SU] U.S.S.R. ............................. 2781356

[51] Int. Cl.³ .................... C12P 13/08; C12N 15/00
[52] U.S. Cl. .................................. 435/115; 435/172; 435/849
[58] Field of Search ............................. 435/115, 172

[56] References Cited

U.S. PATENT DOCUMENTS 3,711,375  1/1973  Nakayama et al. ................. 435/115
4,237,224 12/1980  Cohen et al. ....................... 435/172

*Primary Examiner*—Lionel M. Shapiro
*Attorney, Agent, or Firm*—Steinberg & Raskin

[57] ABSTRACT

The process for producing L-threonine consists in that there is cultivated a producer of L-threonine in the capacity of which is used the *Escherichia coli* strain VNIIgenetika M-1 deposited in the Central museum of commercial microorganisms under the All-Union Research Institute for Genetics and Selection of Commercial Microorganisms at a registration No. IIMIIB-1856. The above strain has been selected on the basis of natural variability of the *Escherichia coli* strain VNIIgenetika VL 334/p YN7), obtained by virtue of the genetic engineering techniques through increasing the dose of mutant genes capable of a higher rate of L-threonine production, by introducing a multicopy hydrid plasmid carrying said genes, into a mutant recipient strain. The abovesaid producer is cultivated on a nutrient medium, containing sources of carbon, nitrogen, and some mineral salts in the presence of an antibiotic penicillin, the resultant biomass being then separated from the culture fluid, whereupon the end product is isolated.

4 Claims, No Drawings

PROCESS FOR PRODUCING L-THREONINE

FIELD OF THE INVENTION

The present invention relates generally to microbiological industry and is concerned more specifically with a process for producing L-threonine. L-threonine is known to be an essential aminoacid extensively applicable as the component of diverse nutritive mixtures of medical use. In addition, L-threonine can be used as an additive to man's food and animals' fodder, as well as a reagent for pharmaceutical and chemical industries.

BACKGROUND OF THE INVENTION

The present state of the art knows a number of diverse processes for producing L-threonine by virtue of submerged cultivation of producer strains of such species as *Brevibacterium flavum, Escherichia coli, Corynebacterium acetoscidophilum, Proteus rettgeri, Serratia marcescensi, Aerobacter aerogenes, Corynebacterium glutamicum*, grown on nutrient media, containing such carbon sources as glucose, fructose, acetic acid, ethanol and doped with some vitamins and aminoacids, or substrates containing these, as well as incorporating nitrogen sources and indispensable mineral salts (cf. British Pat. Nos. 1,223,470; 1,260,995; 1,286,208; French Pat. Nos. 1,573,433; 1,580,549; 1,579,835; 1,603,855; Patent of FRG No. 2,044,907).

The best yield of L-threonine has been achieved from mutant strains of *Br.flavum* producing up to 18 g/l of L-threonine on a glucose medium (cf. Agr. Biol. chem., 1973, 37, 653), up to 40 g/l of L-threonine on an acetic-acid medium (cf. British Pat. No. 1,260,995), and up to 33.8 g/l of L-threonine on an ethanol medium (cf. British Pat. No. 1,286,208). In all these cases use has been made of mutant strains resistant to $\alpha$-amino-$\beta$-hydroxyvaleric acid.

One prior-art process for producing L-threonine is known to consist in submerged cultivation of mutant strains of *Escherichia coli* on nutrient media, containing carbohydrates, nitrogen sources, mineral salts and doped with pure aminoacids and vitamins, or protein mass hydrolyzates containing these. A maximum yield of 10.4 g/l of L-threonine has been obtained on an enzymatic medium for 96 hours of fermentation (cf. British Pat. No. 1,223,470; U.S. Pat. No. 3,711,375; French Pat. Nos. 1,551,414 and 1,580,545).

The mutant strains made use of in the above-mentioned processes exhibit the need for isoleucine, or for isoleucine and methionine (cf. British Pat. No. 1,223,470), or for diaminopimelic acid (cf. U.S. Pat. No. 3,711,375; French Pat. No. 1,551,414).

The processes discussed above are featured, however, by a low level of L-threonine accumulation, particularly on carbohydrate media, as well as a prolonged fermentation period (96 to 120 hours).

One more process for producing L-threonine is known in the art by way of submerged cultivation of an L-threonine producer on a nutrient medium, containing carbon and nitrogen sources and some mineral salts. Used as the producer of L-threonine are some polyauxotrophic *E.coli* mutants, such as the *E.coli* strains ATCC 21272, ATCC 21148, and ATCC 21149, whereas glucose or fructose is applied as a source of carbon. These strains exhibit the need for diaminopimelic acid, isoleucine, or methionine. Thus, for instance, the *E.coli* strain ATCC 21272 needs diaminopimelic acid, methionine, isoleucine, while the strain ATCC 21148 needs diaminopimelic acid and methionine, and the strain ATCC 21149 needs diaminopimelic acid alone. In addition, the cultivation of these strains involves, apart from the above growth factors, also lysin. The cultivation is carried out at 20° at 40° C. When cultivated on a medium, containing 7.5 percent fructose the abovesaid strains produce L-threonine, its concentration in the culture medium first rising, but then starts decreasing with time due to degradation. In order to extend the period of L-threonine accumulation and prevent its concentration from diminishing, some antibiotics are used, such as streptomycin, tetracycline, kanamycin, polymyxin, or their mixtures.

When streptomycin is added 40 hours after the beginning of the fermentation, the latter is prolonged up to 120 hours, and the L-threonine accumulation level amounts to 13.2 g/l, which is the case with the cultivation of the *E-coli* strain ATC 21148 grown on a nutrient medium, containing 7.5 percent fructose and needing diaminopimelic acid and methionine. The amount of the antibiotic added to the nutrient medium ranges within 10 to 1000 mg/l (cf. French Pat. No. 1,579,835).

This process suffers largely from a low average rate of accumulation of the end product in the course of fermentation, which is as low as within 0.15 to 0.20 g/l per hour, thus resulting in a low L-threonine accumulation level and an increased duration of the fermentation process. Moreover, application of this process involves as introduction of some additional components into the medium, such as diaminopimelic acid, methionine or isoleucine, which the producers of the process exhibit the need for.

BRIEF DESCRIPTION OF THE INVENTION

It is an essential object of the present invention to increase the rate of L-threonine accumulation in the culture medium in the course of fermentation of the L-threonine producer.

The abovesaid essential and other objects are accomplished due to the fact that in a process for producing L-threonine by submerged cultivation of the producer, viz., *Escherichia coli* strain on a nutrient medium, containing carbon and nitrogen sources and mineral salts in the presence of antibiotics, followed by separating the biomass from the culture fluid and isolating the end product, according to the invention, used as the producer is the *Escherichia coli* strain VNIIgenetika M-1 deposited in the Central museum of commercial microorganisms at a registration No. IIMIIB and selected on the basis of natural variability of the *Escherichia coli* strain VNIIgenetika VL 334/pyN7), by virtue of the genetic engineering techniques through increasing the dose of mutant genes, cabable of a higher rate of L-threonine production, by introducing a multicopy hybrid plasmid carrying said genes, into a mutant recipient strain, the cultivation being carried out in the presence of penicillin, resistance to which is accounted for by the above hybrid plasmid. It is expedient to introduce pencillin into the original nutrient medium in an amount of 0.1 to 0.5 g/l, which makes it possible to use the culture medium enriched with some nutrients for the fermentation process, whereby the duration of the incipient (nonproductive) stage of fermentation is drastically reduced due to a many-times increase in the specific rate of growth of the culture within that period, without the loss of any principal producer properties. In order to enrich the original nutrient medium use is made of an acid or enzymatic yeast hydrolyzate, or else yeast autolyzate, taken in an amount of 1 to 5 g/l in terms of yeast dry weight; while in order to maintain optimum concentrations of carbon and nitrogen and the pH value in the fermentation medium throughout the fermentation period, a balanced feed-up mixture is periodically added to the nutrient medium, containing an ammoniac solution and a carbon source.

DETAILED DESCRIPTION OF THE INVENTION

The process disclosed in the present invention is carried out as follows.

Used as the producer strain is the *E.coli* strain VNIIgenetika M-1 selected on the basis of natural variability of the original *E.coli* strain VNIIgenetika VL 334/pyNT/. The process for producing the *E.coli* strain VNIIgenetika VL 334/pyN7) consists in that a fragment of the chromosome of the donor *E.coli* strain VNIIgenetika MG-442, obtained with the help of the endonuclease containing all the genes of the threonine operon, is combined by methods well-known in the art with a vector DNA molecule, in the capacity of which is used the plasmid pBR 322. The result is the formation of a hybrid plasmid. The thus obtained hybrid plasmid consists of one molecule of the plasmid pBR 322 and the abovesaid fragment of the DNA of the donor strain chromosome, renders the cells penicillin-resistant and may occur in the cells in an amount of 40 to 50 copies at the stage of logarithmic growth. Then the resultant hybrid plasmid is used for transforming the cells of the recipient *E.coli* strain VL 334 which has some mutations capable of blocking the synthesis of L-threonine and an adjacent pathway of L-threonine methabolism in said strain. The mutations impart a selective advantage to the cells containing an amplified hybrid plasmid in the course of cultivation in minimal glucose-salt medium. As a result, the L-threonine-producing *E.coli* strain VNIIgenetika VL 334/pYN7/ is obtained, which is deposited in the Central museum of commercial microorganisms under the All-Union Research Institute for Genetics and Selection of Commercial Microorganisms at a registration No. IIMIIM B-1684.

The thus-obtained strain has then been inoculated to an agar-doped culture medium, and a great many of individual colonies have been checked for ability to produce L-threonine on a minimal glucose-salt nutrient medium and to retain the plasmid in the course of fermentation, with the result that the *E.coli* strain VNIIgenetika M-1 has been isolated.

The *Escherichia coli* producer strain VNIIgenetika M-1 features the following characteristics.

Morphology. Lightly mobile Gram-negative slender bacilli 1.5 to 2 mm long, with rounded ends.

CULTURAL AND PHYSIOLOGICAL FEATURES

Beef-extract agar. After a 24-hour growth at 37° C. the strain forms round whitish semitransparent colonies 2 to 3 mm in diameter; the surface is smooth, the edges are even or lightly wavy, the centre of the colony is raised a little, the structure is homogeneous, the consistency is pastelike, readily emulsifiable.

Minimal agar-doped nutrient medium (Adams's) with glucose. After a two-day growth at 37° C. the strain forms round greyish-white colonies 1 to 1.5 mm in diameter, with even edges, lightly convex, with a homogeneous internal structure, with a lustrous surface; in 4 or 5 days the colonies acquire mucoid consistency.

Growth in beef-extract broth. After a 24-hour growth at 37° C. develops strong uniform turbidity; light precipitate settles down, having a characteristic odour. The doubling time is 33 minutes.

Growth in Adams's liquid minimal medium. After a two-day growth at 37° C. under aeration strong uniform turbidity is developed.

The doubling time is 240 minutes.

Growth of deep-stub culture on beef-extract agar. Good growth throughout the stub culture.

Gelatin liquefying ability—none.

Growth on milk. Good growth accompanied by milk coagulation.

Indole forming ability—available.

Growth on various carbohydrates. Good growth on glucose, lactose, mannose, galactose, xylose, fructose, glycerol and mannitol, with the formation of an acid and gas.

Resistance to antibiotics. Penicillin-resistant.

The strain is not pathogenic.

Plasmid content. At the logarithmic stage of growth the cells contain about 40 to 50 copies of the plasmid pYN7 (with a molecular weight of 5.7 Megadalton), which ensures the penicillin-resistance of the strain carries the genes of the threonine operon.

The *E.coli* strain VNIIgenetika M-1 selected from the inoculated cultures of the *E.coli* strain VNIIgenetika VL 334/pYN7), differs from the original strain in a notable mucoid nature of the surface of the colonies, an increased threonine-producing capacity, higher stability when grown on media doped with nutritional additives, i.e., an ability of the cells to retain the principal properties (the threonine producing ability and penicillin resistance) after cultivation under such conditions. The comparative characteristics of the abovesaid strains are given in the table below.

TABLE

Comparative characteristics of the *E. coli* strain VNIIgenetika M-1 and the original *E. coli* strain VNIIgenetika VL 334/p$^y$N7) as to the ability of the cell population to retain their principal properties (threonine producing ability and penicillin resistance) after cultivation under various conditions

| | Occurrence of cells retaining their principal properties after having cultivated (in percent) | |
|---|---|---|
| Strain | in glucose-salt medium | in beef-extract broth |
| *E. coli* strain VNIIgenetika VL 334/p$^y$N7/ | 72 to 98 | 2 to 42 |
| *E. coli* strain VNIIgenetika M-1 | 88 to 100 | 82 to 98 |

The cultures were grown on a shaker at 37° C. on the media specified in the table. After ten generations had been obtained, the cultures were seeded on dishes, containing agar-doped Hottinger broth to obtain individual colonies. Then at least 100 colonies in each experiment was checked, by means of a replicator, for penicillin resistance and for threonine producing ability.

As it is obvious from the data tabulated above, the cell populations of both strains, after having been cultivated on a glucose-salt medium, are found to retain their threonine-producing ability at a nearly equal level, i.e., they prove to be stable under these conditions. However, after having been cultivated on a medium rich in nutrients (beef-extract broth), the number of cells retaining the threonine producing ability is much greater in the novel E.coli strain VNIIgenetika M-1 as compared to the original strain, that is, the novel strain is more stable under enriched-medium conditions.

This property of the E.coli strain VNIIgenetika M-1, alongside with introducing penicillin into the medium, resistance to which is accounted for by the hybrid plasmid, make it possible to use nutrient additives in the course of cultivation, which accelerate much the microorganism growth. Thus, for instance, the generation time of the E.coli strain VNIIgenetika M-1 cultivated on a glucose-salt medium is 240 minutes, whereas the generation time for an enriched medium equals 30 to 40 minutes. In its turn higher rate of the strain growth on an enriched medium enables one to rule out the stages of preparing the inoculum in the flasks and inoculators from the process flowsheet, as well as to cut down the fermentation period.

The cultivation process is carried out as follows.

The inoculum of the culture of the E.coli microorganism, strain VNIIgenetika M-1 is grown for 40 to 50 hours on an agar-doped minimal nutrient medium, containing penicillin (500 gamma/ml); then the cells of the cultura are washed out of the surface of the agar slant with physiological saline. The thus-obtained cell suspension is used for inoculation of the fermentation medium. An initial cell concentration in the process fermenter may be about $2$ to $5 \times 10^6$ to $10^7$ cells per ml. The original nutrient medium contains glucose, mineral nitrogen, salts, penicillin and nutritional additives in the form of protein mass hydrolyzates, such as acid hydrolyzates, autolyzates or enzymatic hydrolyzates of yeast. The initial pH value of the medium is equal to 7.0 or 7.2, and is then self-maintained within these limits throughout the fermentation period by a pH monitor, through adding a balance feed-up, containing ammoniac (an aqueous solution) and glucose. Inasmuch as dropping of the pH value of the medium in the course of cultivating the L-threonine producer is accounted for by a reduced ammoniac (nitrogen) concentration the medium due to utilization of the latter by the producer, whereas the ratio between the nitrogen and glucose utilization rates remains nearly the same, the ratio between the amount of the given components in the nutrient medium must correspond to the ratio between the rates of utilization of these components by the producer culture. This is achieved by introducing the abovesaid feed-up additive in the course of fermentation. The process is carried out under continuous aeration and stirring, the temperature being maintained within 30° to 40° C. The fermentation time is 40 to 50 hours.

Upon terminating the fermentation process up to 30 g/l of threonine is accumulated in the culture fluid. The isolation of L-threonine is carried out as follows.

The producer cell biomass is separated either by centrifugation or by filtration, after having preliminary been treated with calcium oxide and orthophosphoric acid. Making due account of the content of L-threonine and cations in the native solution, as well as of pigmented compounds, the native solution is passed through a row of tandem arranged columns, packed with a clarifying sorbent to absorb the pigmented compounds, and with sulphocationite in the H-form to provide sorption of the cations and L-threonine. The thus-sorbed L-threonine is then eluated from the sulphocationite-packed column, with an ammoniac solution. The eluate fractions containing a great majority of L-threonine, are evaporation-concentrated in vacuo, then cooled and L-threonine is crystallized. To accelerate the crystallization some alcohol may be added. The thus-obtained L-threonine is chromatographically homogeneous and contains 97 to 99 percent of the principal matter. Thus, in order to obtain medical-use preparations, the product is merely recrystallized. Such preparations can be applied in media for tissue cell cultivation. The yield of the end product according to the above-described process, equals 80 to 95 percent. With higher L-threonine concentration in the culture fluid (above 18 g/l) and a relatively low content of impurities, L-threonine may be isolated without resorting to sorption on the ionites. To this end, the clarified solution of the end product is evaporation-concentrated in vacuo at low temperatures, whereupon L-threonine is crystallized at a reduced temperature with or without adding some ethanol. Upon recrystallization L-threonine is obtained, featuring 99 percent of the principal matter.

The proposed process is more efficient when compared to every process for producing L-threonine on carbohydrate media known heretofore, and makes it possible to obtain a concentration of L-threonine in the culture fluid up to 30 g/l, without any admixtures of other aminoacids, and to reduce the duration of the fermentation process to 40 hours.

An average rate of L-threonine accumulation in the course of fermentation amounts of 0.75 g/l per hour, which is five times that of L-threonine accumulation according to the known process.

To promote understanding given below are the following examples of practical embodiment of a process for producing L-threonine, disclosed in the present invention.

EXAMPLE 1

The inoculum of the E.coli producer strain VNIIgenetika M-1 is cultivated for 43 hours on an agar-doped minimal glucose-salt nutrient medium of the following composition (in g/l): glucose, 5.0; $NH_4Cl$, 1.0; $KH_2PO_4$, 1.5; $Na_2HPO_4$, 3.5; $MgSO_4.7H_2O$; 0.1; penicillin, 500 gamma/ml; agar—agar, 20.0; distilled water being the balance; the pH value ranging within 7.0 to 7.2. Glucose and penicillin are sterilized separately and added to a molten medium before its cooling and inoculation. The grown culture is washed off with sterile tap water, and the thus-obtained cell suspension is used for seeding the fermenters. The initial concentration of the producer cells in the fermentation medium ranges within $10^6$ to $10^7$ cells per ml.

The fermentation process is carried out in a 0.5 l capacity laboratory fermenter. The composition of the basic fermentation nutrient medium is as follows (in volume percent):

| | |
|---|---|
| $(NH_4)_2SO_4$ | 1.5 |
| $K_2HPO_4$ | 0.2 |
| $MgSO_4$ | 0.04 |
| Acid yeast hydrolyzate (in terms of yeast dry weight) | 0.3 |
| Froth killer | 0.1 |
| Water being the balance. | |

The nutrient medium is sterilized along with the fermenter, whereupon added to the medium are sterile glucose (2 percent) and penicillin (0.5 g/l).

The fermentation process is carried out at 35° to 37° C. and is accompanied by adding a balanced feed-up in the form of a mixture, containing ammoniac (2.5 to 2.7 percent) and glucose in a 35-percent concentration. The feed-up mixture is added in response to a signal delivered by the pH monitor. The pH value is maintaining within 7.0 to 7.2. After a 40-hour fermentation time L-threonine is accumulated in the culture fluid in an amount of 30 g/l. An average rate of L-threonine accumulation is 0.75 g/l per hour. The amount of glucose spent for the synthesis of L-threonine is 6 g per gramm of L-threonine.

Next L-threonine is isolated from the culture fluid. To this end, added to 300 ml of the culture fluid having a concentration of L-threonine equal to 30 g/l, under constant stirring is 3 g calcium oxide, whereupon phosphoric acid is introduced to bring the pH value to 5.6; then the solution is heated to 60° C., kept for 10 minutes, and the biomass is filter-separated in vacuo. The thus-obtained native solution, featuring an optical density of 0.4 at 525 nm in a 1-cm cuvette, is passed through a column packed with 50 ml clarifying resin, and the clarified solution (having an optical density of 0.08) is passed through a column packed with 150 ml sulphocationite in the H-form, whereupon the column is washed with 300 ml water. The thus-sorbed L-threonine is eluated with a 3-percent ammoniac solution, the eluate is evaporation-concentrated in vacuo till a 25-percent dry matter content, some ethanol is added in a ratio of 1:1, and the mixture is allowed to crystallize for 10 hours at 0° C. to +5° C. The L-threonine crystals are filtered out, washed and dried to obtain 8.1 g L-threonine (the yield percentage being 90). A chromatographic analysis by the thin-layer techniques (with 10 gamma of the preparation applied to the chromatogram) demonstrates complete freedom from any other aminoacids.

EXAMPLE 2

The inoculum of the *E.coli* producer strain VNIIgenetika M-1 is prepared as in Example 1.

The fermentation process is carried out in a 0.5 l capacity fermenter. The composition of the original nutrient medium is similar to that described in Example 1 with the exception that used as a nutritional additive is an enzymatic yeast hydrolyzate (instead of an acid yeast hydrolyzate), in an amount of 0.5 percent in terms of yeast dry weight.

The fermentation conditions are similar to those described in Example 1. After a 41-h fermentation time L-threonine is accumulated in the culture fluid in an amount of 29 g/l. An average rate of L-threonine accumulation is 0.71 g/h. Then L-threonine is isolated from the culture fluid.

To this aim, the producer cells are centrifugation-separated from the culture fluid, whereupon 30 ml L-threonine native solution containing 7.5 percent dry matter and featuring an optic density of 0.6 at 525 nm, is evaporation-concentrated in vacuo at 50° C. till a volume of 50 ml; next the same amount of ethanol is added, and L-threonine is allowed to crystallize for 5 hours at 0° C. The thus-obtained crystals are filtration-separated, washed with 15 ml ethanol and dried to give 6.1 g L-threonine. A chromatographic analysis by the thin-layer techniques (with 10 gamma of the preparation applied to the chromatogram) shows no other aminoacids.

EXAMPLE 3

The inoculum of the *E.coli* producer strain VNIIgenetika M-1 is prepared as in Example 1.

The fermentation process is carried out in a 2-m$^3$ fermenter. The composition of the original nutrient medium is similar to that described in Example 1, with the exception that used a nutritional additive to the nutrient medium is yeast autolyzate in an amount of 0.4 percent in terms of yeast dry weight, while the penicillin content is 0.2 g/l.

The initial concentration of the producer cells in the fermentation medium is within $10^3$ to $10^4$ cells per ml.

After a 43-hour fermentation time 18 g/l of L-threonine is accumulated in the culture fluid. The glucose consumption rate is the same as in Example 1. An average rate of L-threonine accumulation is 0.42 g/l per hour.

The isolation of the end product is carried out as in Example 1. The yield of L-threonine is 80 percent.

What we claim is:

1. A process for producing L-threonine, consisting in that an L-threonine producer is cultivated, in the capacity of which is used the *Escherichia coli* strain VNIIgenetika M-1 deposited in the Central museum of commercial microorganisms under the All-Union Research Institute for Genetics and Selection of Commercial Microorganisms at a registration No. IIMIIB-1856, said strain having been selected on the basis of natural variability of the *Escherichia coli* strain VNIIgenetika VL 334/pYN7), obtained by virtue of the genetic engineering techniques through increasing the dose of mutant genes capable of a higher rate of L-threonine production, by introducing a multicopy hybrid plasmid carrying said genes, into a mutant recipient strain, said producer being cultivated at 30° to 40° C. on a nutrient medium, containing carbon and nitrogen sources and some mineral salts, in the presence of an antibiotic penicillin, resistance to which is accounted for by said hybrid plasmid; the cultivation having been terminated, the resultant biomass is separated from the culture fluid, and the end product is isolated.

2. A process as claimed in claim 1, wherein said cultivation is carried out in the presence of penicillin, taken in an amount of 0.1 to 0.5 g/l.

3. A process as claimed in claim 1, wherein said cultivation is carried out on a nutrient medium, containing a protein mass hydrolyzate, selected from the group, containing yeast hydrolyzate, enzymatic yeast hydrolyzate, and yeast autolyzate, taken in an amount of 0.1 to 0.5 percent in terms of yeast dry weight.

4. A process as claimed in claim 1, wherein with a view to maintaining optimum carbon and nitrogen concentrations and constant pH value throughout the cultivation process, a mixture is periodically introduced into the culture medium, said mixture containing an ammoniac solution and a carbon source.

* * * * *